United States Patent [19]

Sherif et al.

[11] Patent Number: 4,487,749
[45] Date of Patent: Dec. 11, 1984

[54] DICALCIUM PHOSPHATE DIHYDRATE HAVING IMPROVED MONOFLUOROPHOSPHATE COMPATIBILITY AND PROCESS FOR THE PREPARATION THEREOF

[75] Inventors: Fawzy G. Sherif, Stony Point; Helmut W. Majewski, Nyack; Francis A. Via, Yorktown Heights, all of N.Y.

[73] Assignee: Stauffer Chemical Company, Westport, Conn.

[21] Appl. No.: 511,727

[22] Filed: Jul. 8, 1983

Related U.S. Application Data

[63] Continuation of Ser. No. 336,215, Dec. 31, 1981, abandoned.

[51] Int. Cl.$^3$ ............................................. C01B 25/32
[52] U.S. Cl. .................................... 423/309; 423/267; 423/308

[58] Field of Search ....................... 423/308, 309, 267

[56] References Cited

U.S. PATENT DOCUMENTS

| | | | |
|---|---|---|---|
| 2,036,760 | 4/1936 | Knox | 423/309 |
| 3,012,852 | 12/1961 | Nelson | 423/309 |
| 3,294,486 | 12/1966 | Cremer et al. | 423/309 |
| 4,312,843 | 1/1982 | Monty et al. | 423/267 |

Primary Examiner—Gary P. Straub
Assistant Examiner—Wayne A. Langel
Attorney, Agent, or Firm—Hensley M. Flash

[57] ABSTRACT

Dicalcium phosphate dihydrate compositions having improved monofluorophosphate compatibility are prepared by reacting a lime slurry with phosphoric acid to form a monocalcium phosphate solution, and then further reacting the monocalcium phosphate solution with additional lime slurry to a pH in the range of from above about 2.2 to below about 5.5.

4 Claims, No Drawings

DICALCIUM PHOSPHATE DIHYDRATE HAVING IMPROVED MONOFLUOROPHOSPHATE COMPATIBILITY AND PROCESS FOR THE PREPARATION THEREOF

This is a continuation of application Ser. No. 336,215, filed Dec. 31, 1981, now abandoned.

BACKGROUND OF THE INVENTION

The present invention relates to dicalcium phosphate compositions having improved monofluorophosphate compatibility, and to a process for the preparation thereof.

Dicalcium phosphate dihydrate has been used as a dental polishing agent in toothpastes and powders for many years.

This material is typically produced by first reacting a slaked lime slurry with phosphoric acid to form a dicalcium phosphate dihydrate precipitate, and then separating the dicalcium phosphate dihydrate precipitate from the mother liquor, after which it is dried and milled to form the final product as a fine powder.

One serious problem which was initially encountered in the use of dicalcium phosphate dihydrate in toothpaste was the tendency of the dicalcium phosphate to "set-up" and become lumpy. When this occurs in toothpaste formulations, it makes it difficult to extrude the toothpaste from the tube in which it is usually packaged.

A second problem was encountered with the advent of the use of monofluorophosphate additives in toothpaste formulations. It was found that the monofluorophosphate components would react with the dicalcium phosphate whereby the monofluorophosphate component was converted from a water-soluble form to an insoluble form. Since the beneficial effect of monofluorophosphate additives in toothpaste are understood to be derived principally from the water-soluble form, it has become important to develop toothpaste formulations which permit an effective amount of monofluorophosphate component to remain in the water-soluble state.

The term "monofluorophosphate-compatibility" has been used as a term-of-art to describe the tendency of such formulations to permit the monofluorophosphate component to remain in the water soluble state.

The monofluorophosphate compatibility of a particular formulation may be determined by a variety of methods. Preferably, the monofluorophosphate compatibility of a formulation is determined by actually preparing the formulation, placing it in storage for a predetermined period of time under controlled conditions, and then determining the amount of water-soluble monofluorophosphate which remains in the formulation after having been stored under these conditions. Alternatively, a simulated formulation, such as the dicalcium phosphate dihydrate to be tested, glycerine and a known amount of a monofluorophosphate component, such as sodium monofluorophosphate can be "quick aged" by maintaining it at an elevated temperature for one or more hours, and then determining the amount of water-soluble monofluorophosphate remaining after such conditioning. There are, of course, many other methods for measuring the relative monofluorophosphate compatibility of various samples of dicalcium phosphate dihydrate.

U.S. Pat. No. 2,287,699 teaches that dicalcium phosphate dihydrate may be stabilized by adding a small amount of an alkali metal pyrophosphate to the mother liquor, at a controlled pH, during the preparation of the dicalcium phosphate. Specifically, it is taught that after precipitation of the dicalcium phosphate in the mother liquor, a small amount of alkali metal pyrophosphate should be added and the entire slurry then heated for a short period of time, while maintaining the pH of the mother liquor above 7.

Alternatively, the precipitate may be treated during the subsequent washing step.

It is also known to those skilled in the art that other forms of pyrophosphate can also be used to stabilize the dicalcium phosphate.

U.S. patent application Ser. No. 106,637 now U.S. Pat. No. 4,312,843 teaches a method for preparing dicalcium phosphate dihydrate compositions having improved monofluorophosphate compatibility which involves the addition of pyrophosphoric acid to the reaction mixture and terminator of the reaction within a very limited pH range of from about 4.9 to about 5.5.

Suprisingly and unexpectedly in view of the teachings of the prior art it has now been found that high monofluorophosphate compatibility can be obtained by terminating the reaction by which dicalcium phosphate dihydrate is formed at any pH in the range of from above about 2.2 to below about 5.5, and that the addition of pyrophosphoric acid is not essential for the achievement of high monofluorophosphate compatibility.

SUMMARY OF THE INVENTION

In accordance with the present invention there is now provided a process for preparing dicalcium phosphate dihydrate having improved monofluorophosphate compatibility which comprises the steps of (a) reacting a slaked lime slurry with phosphoric acid to form a monocalcium phosphate solution; (b) further reacting the monocalcium phosphate solution with additional slaked lime slurry to form a dicalcium phosphate dihydrate slurry having a pH ranging from above about 2.2 to below about 5.5; and (c) separating the dicalcium phosphate dihydrate from the slurry.

DETAILED DESCRIPTION OF THE INVENTION

In accordance with the present invention, it has been discovered that improved monofluorophosphate compatibility can be achieved by terminating the reaction by which dicalcium phosphate dihydrate is formed at a pH ranging from above about 2.2 to below about 5.5. In a particularly-preferred embodiment, the reaction is terminated at a pH ranging from about 3.0 to about 3.5.

Although it had been found by others that the addition of pyrophosphoric acid to the reaction mixture in combination with termination of the reaction at a pH ranging from about 4.9 to about 5.5 resulted in improved monofluorophosphate compatibility, we have now found that improved compatibility can be achieved without the pyrophosphoric acid.

The addition of pyrophosphoric acid can be helpful in improving the stability of the product, but is not essential for the achievement of monofluorophosphate compatibility. In this regard, acids other than pyrophosphoric may also be added. The acids which may be added include, but are not limited to orthophosphoric, polymetaphosphoric, cyclic trimeta- and tetrameta-phosphoric acids, triphosphoric, sulfuric, tetraphosphoric acid and the like. When acid addition is used, the acid may be added during, or after the addition of the lime slurry to the monocalcium phosphate solution although it is preferable to add it after lime slurry addition has been completed. The amount added can range from about 0.1% to about 1.0% by weight of dicalcium phosphate dihydrate to be prepared.

The reaction by which the dicalcium phosphate dihydrate is formed in accordance with the present invention is terminated at a pH above about 2.2 and below about 5.5, whether acid-addition is used or not.

It has been found that the formation of dicalcium phosphate dihydrate crystals during addition of the lime slurry to the monocalcium phosphate solution begins at a pH of about 2.2. Yield at this low pH, however, is relatively low.

The dicalcium phosphate dihydrate crystals which are formed at pH's between about 2.2 and about 3.2 appear to have a high degree of monofluorophosphate compatibility, but yield increases as more lime slurry is added to increase the pH. Thus, higher pH's are accompanied by higher yields.

It appears that the crystals which are formed at pHs above about 3.3 have lower monofluorophosphate compatibility than those formed at lower pHs, but the overall monofluorophosphate compatibility of the total mixture of crystals formed remains quite high even at a pH of about 4.9 and acceptably-high monofluorophosphate compatibility can be obtained at terminal pHs as high as 5.5. When the reaction is terminated at the higher end of the range just discussed, it is preferable to add a small amount of an acid to the slurry following lime addition, to obtain a lower "final" pH, because the lower "final" pHs tend to result in better monofluorophosphate compatibilities. Where, however, yield can be sacrificed in favor of further improved monofluorophosphate compatibility, lower terminal pHs, especially those of about 3.3 or lower, are preferred.

The lime which is used in the practice of the present invention is the same type rotary kiln lime or shaft kiln lime as is used in conventional dicalcium phosphate processes.

The slaked lime slurry is prepared by mixing lime with either water or recycled mother liquor (i.e., that which remains after removal of the dicalcium phosphate dihydrate product from the final slurry), or both, in amounts of from about 100 to about 150 grams CaO/liter and at a temperature ranging from about 70° C. to about 74° C. At higher concentrations the mixture can become a gelatinous mass which can be difficult to handle, while at concentrations below the range specified the process "payload" will be unnecessarily reduced.

The slaked lime slurry is then added to phosphoric acid to form a monocalcium phosphate solution.

The acid which is used is preferably a food grade phosphoric acid, preferably at an initial concentration of about 85%. Varying amounts of recycled mother liquor may also be added to the lime slurry and phosphoric acid, with the specific amount in each case being determined in accordance with the preferences of the individual practitioner. The compositional range of the monocalcium phosphate solution will be approximately as follows:

|        | High (Wt. %) | Low (Wt. %) |
|--------|--------------|-------------|
| CaO    | 4            | 2           |
| $P_2O_5$ | 22         | 12          |
| pH     | 2            | 1           |

These ranges are set forth as examples of those which are typical, and are in no way intended to be limitations on the scope of the present invention. Those skilled in the art will understand that higher and lower amounts may also be used, provided that the reaction mixture meets the requirements of the practitioner.

When the lime slurry and phosphoric acid are brought together under the conditions specified above, a reaction will ensue and a monocalcium phosphate solution will be formed. The essential completion of the reaction will be indicated by a steady-state pH of from about 1.0 to about 2.0.

The preparation of the monocalcium phosphate solution can be carried out as a continuous, batch or semi-batch process; as can the overall process.

Once the monocalcium phosphate solution has been formed, additional slaked lime slurry is added to form the dicalcium phosphate dihydrate slurry. This reaction is exothermic and external cooling is required to control the reaction temperature. The reaction temperature should be controlled at or below about 50° C.

Once the dicalcium phosphate dihydrate slurry has been formed as described above, the dicalcium phosphate dihydrate product is separated from the mother liquor. The mother liquor may then be recycled to the beginning of the process, or discarded.

The separation of the dicalcium phosphate dihydrate from the slurry can be accomplished by any of several conventional techniques. These techniques include, but are not limited to, decantation, centrifugation, filtration and the like, although decantation is preferred because of its simplicity.

Once the dicalcium phosphate dihydrate is separated from the slurry, it can be dried, milled and mixed with a stabilizer.

The stabilizers which are typically added to dicalcium phosphate dihydrate are intended to prevent the "caking" and "lumping" which occurs in unstabilized dicalcium phosphate dihydrate as a result of dehydration. There are many stabilizers known to be useful for this purpose. These include, but are not limited to dimagnesium phosphate, trimagnesium phosphate, magnesium stearate and magnesium sulfate. The amount of stabilizer added ranges from about 0.5% to about 5.0% by weight of dicalcium phosphate dihydrate. Preferred stabilizers for use in conjunction with the practice of the present invention are dimagnesium phosphate trihydrate, trimagnesium phosphate octahydrate, and mixtures thereof.

It is preferred to add the stabilizer to the dicalcium phosphate dihydrate by dry-blending these two components after the dicalcium phosphate dihydrate has been dried or after it has been dried and milled. It is however, within the scope of the invention to add the stabilizer to the product slurry before separating the dicalcium phosphate dihydrate therefrom; or to the "wet" dicalcium phosphate dihydrate prior to drying and milling.

In order that the present invention be more fully understood, the following examples are given by way of illustration. No specific details or enumerations contained therein should be construed as a limitation of the present invention except insofar as they appear in the appended claims.

EXAMPLE I

A slaked lime slurry prepared from rotary kiln lime and distilled water (about 125 grams CaO/ liter) was slowly added, with stirring to 34% food grade phosphoric acid to form a clear solution of monocalcium phosphate having about 18% $P_2O_5$ and 3% CaO and a pH of about 1.0.

Additional lime slurry was then added, with stirring, to the solution until the pH reached 6.3. Stirring was continued for about 30 minutes, at which time a final pH of 6.8 was measured. The temperature during the entire process was maintained at 40°–42° C. by means of a temperature-controlled water bath.

The resultant dicalcium phosphate dihydrate was then separated by filtration, dried at 50° C., milled and blended with 2% wt. trimagnesium phosphate. A standard toothpaste formulation having an initial monofluorophosphate content of 1000 ppm(expressed as ppm $F^-$) was then prepared using the dicalcium phosphate dihydrate, and aged for 3 weeks at 49° C. The amount of water-soluble monofluorophosphate remaining was measured at the end of the 3 weeks. The results are shown in Table I.

EXAMPLE II

Example I was repeated, except that the terminal pH was 5.8 and final pH was 6.3.

EXAMPLE III

Dicalcium phosphate dihydrate was prepared as in the previous Examples, except that the lime slurry addition was terminated at a pH of 5.3 (terminal pH) and the final pH (i.e., the pH after stirring for 30 minutes after termination of lime slurry addition) was 6.0. The results are shown in Table I.

EXAMPLE IV

Dicalcium phosphate dihydrate was prepared as in the previous Examples, except that the terminal pH was 3.2 and the final pH was 3.0. The results are shown on Table I.

EXAMPLE V

Example IV was repeated. The terminal and final pHs were the same. The results are shown on Table I.

EXAMPLE VI

Dicalcium phosphate dihydrate was prepared as in Example I, except that 0.2 wt. % orthophosphoric acid by weight of final product was added after termination of lime slurry addition. When the lime slurry addition was terminated, and before the acid was added, the pH was found to be 5.8 (i.e., terminal pH). After the acid was added and the slurry stirred for an additional 30 minutes, the pH was found to be 5.7 (i.e., final pH). The results are shown on Table I.

EXAMPLE VII

Example 6 was repeated, except that the terminal and final pHs were both 5.6.

EXAMPLE VIII

Example 6 was repeated except that pyrophosphoric acid was used instead of orthophosphoric acid, and the terminal and final Ph's were 5.8 and 5.4 respectively.

EXAMPLE IX

Example 8 was repeated; the terminal and final pH's were the same.

EXAMPLE X

Example 8 was repeated a second time; the terminal and final pH's were again the same.

The control samples used in each of these Examples were all taken from the identical source.

TABLE I
MONOFLUOROPHOSPHATE COMPATIBILITY OF DICALCIUM PHOSPHATE DIHYDRATE

| Example No. | pH Terminal | pH Final | Compatibility[1] Product | Compatibility[1] Control[2] |
|---|---|---|---|---|
| 1 | 6.3 | 6.8 | 635 | 660 |
| 2 | 5.8 | 6.3 | 655 | 660 |
| 3 | 5.3 | 6.0 | 630 | 653 |
| 4 | 3.2 | 3.0 | 800 | 700 |
| 5 | 3.2 | 3.0 | 776 | 700 |
| 6 | 5.8 | 5.7 | 700 | 660 |
| 7 | 5.6 | 5.6 | 710 | 653 |
| 8 | 5.8 | 5.4 | 720 | 653 |
| 9 | 5.8 | 5.4 | 640 | 625 |
| 10 | 5.8 | 5.4 | 650 | 625 |

[1] Monofluorophosphate compatibility is expressed as ppm $F^-$
[2] The control used in all Examples was obtained from the identical source.

These results show that dicalcium phosphate dehydrate having high levels of monoflurophosphate can be prepared using final pHs within the range described herein and that these high compatibility levels can be achieved with or without the addition of pyrophosphoric acid.

We claim:
1. A process for preparing dicalcium phosphate dihydrate having improved monofluorophosphate compatibility which consists essentially of the steps of:
   (a) reacting a slaked lime slurry with phosphoric acid to form a monocalcium phosphate solution;
   (b) further reacting said monocalcium phosphate solution with additional slaked lime slurry to form a dicalcium phosphate dihydrate slurry having a final pH ranging from above about 2.2 to below about 5.5;
   (c) separating the dicalcium phosphate dihydrate from said slurry.
2. The process of claim 1 wherein an acid other than pyrophosphoric acid is added during or after step (b).
3. The process of claim 2 wherein said acid is an acid selected from the group consisting of orthophosphoric acid, polymeta phosphoric acid, tri and tetrameta phosphoric acids, sulfuric acid, triphosphoric and tetraphosphoric acids.
4. The process of claim 1 wherein said pH ranges from above about 3.0 to about 3.5.

* * * * *